United States Patent
Hull et al.

[11] Patent Number: 5,897,588
[45] Date of Patent: Apr. 27, 1999

[54] CORONARY STENT AND METHOD OF FABRICATING SAME

[76] Inventors: Cheryl C. Hull; Michael D. Crocker, both of 1220 S. Neveen La., Anaheim, Calif. 92804

[21] Appl. No.: 08/818,621
[22] Filed: Mar. 14, 1997
[51] Int. Cl.$^6$ .................................................... A61F 2/06
[52] U.S. Cl. .................................................. 623/1; 623/12
[58] Field of Search .................................. 623/1, 11, 12; 606/194, 195, 198

[56] References Cited

U.S. PATENT DOCUMENTS

| | | | |
|---|---|---|---|
| 5,549,663 | 8/1996 | Cottone, Jr. ............................ | 606/195 |
| 5,575,818 | 11/1996 | Pinchuk .................................. | 606/195 |
| 5,593,412 | 1/1997 | Martinez et al. ...................... | 606/194 |
| 5,707,387 | 1/1998 | Wijay ..................................... | 623/1 |
| 5,716,396 | 2/1998 | Williams, Jr. ......................... | 623/1 |

Primary Examiner—Debra S. Brittingham
Attorney, Agent, or Firm—Stetina Brunda Garred & Brucker

[57] ABSTRACT

An expandable intraluminal stent having a tubular shaped member having first and second ends defining an axial passageway therethrough. The tubular shaped member has a multiplicity of slots helically formed thereabout that are preferably provided in rows wherein the slots of each row are arranged in an end to end fashion. The tubular shaped member is initially disposable in a radially collapsed configuration such that the device may be passed into the lumen of a blood vessel, and subsequently expand to an operative configuration wherein it will frictionally engage the surrounding blood vessel wall to hold the device in fixed position within the blood vessel lumen. In an alternative embodiment, the stent is designed to accommodate a bifurcated vessel having a collateral vessel extending therefrom.

9 Claims, 2 Drawing Sheets

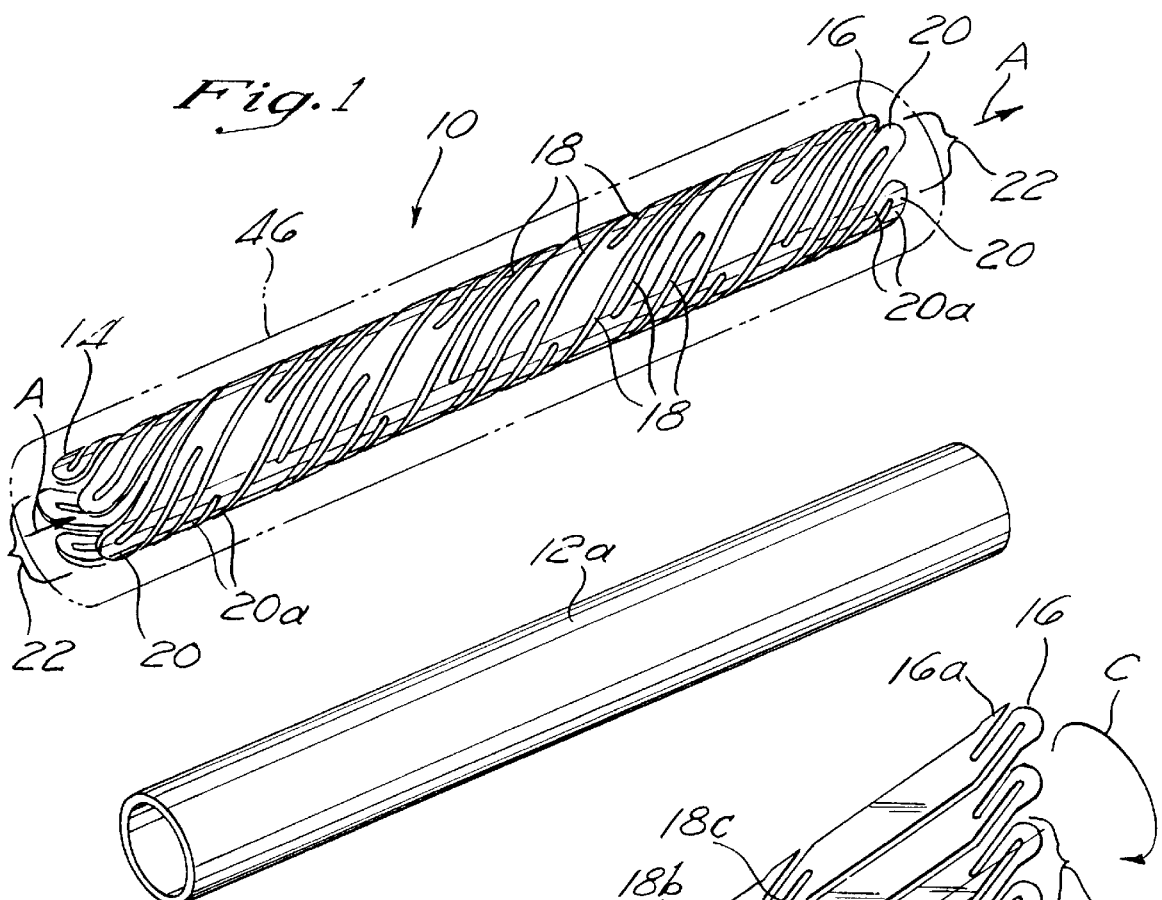
Fig. 1
Fig. 2
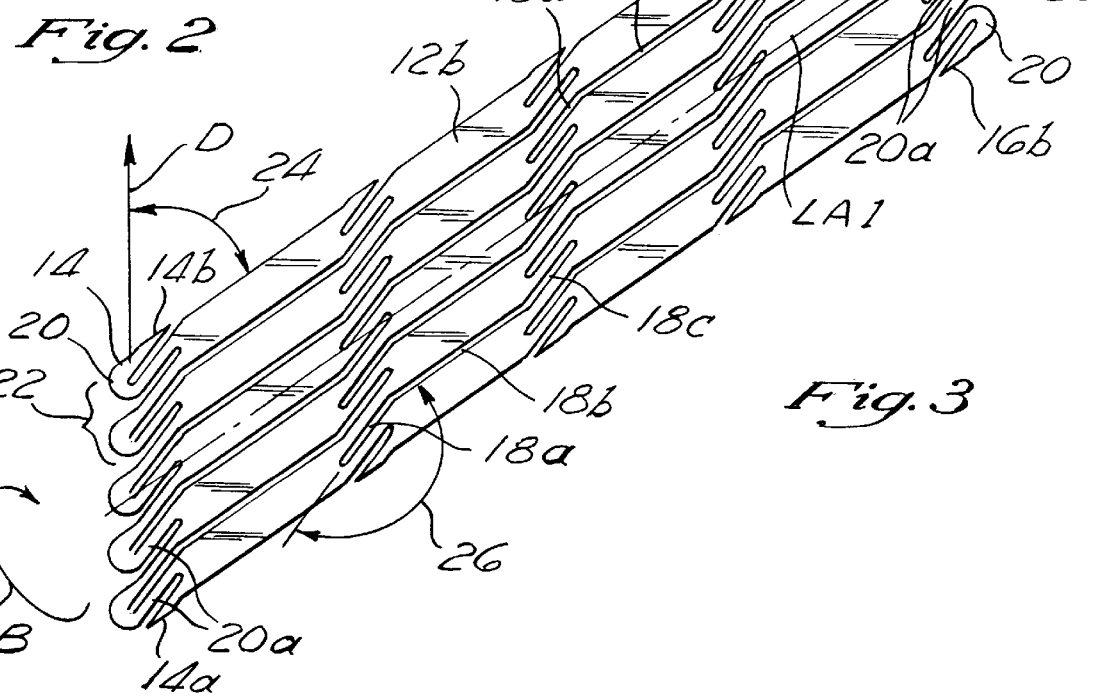
Fig. 3

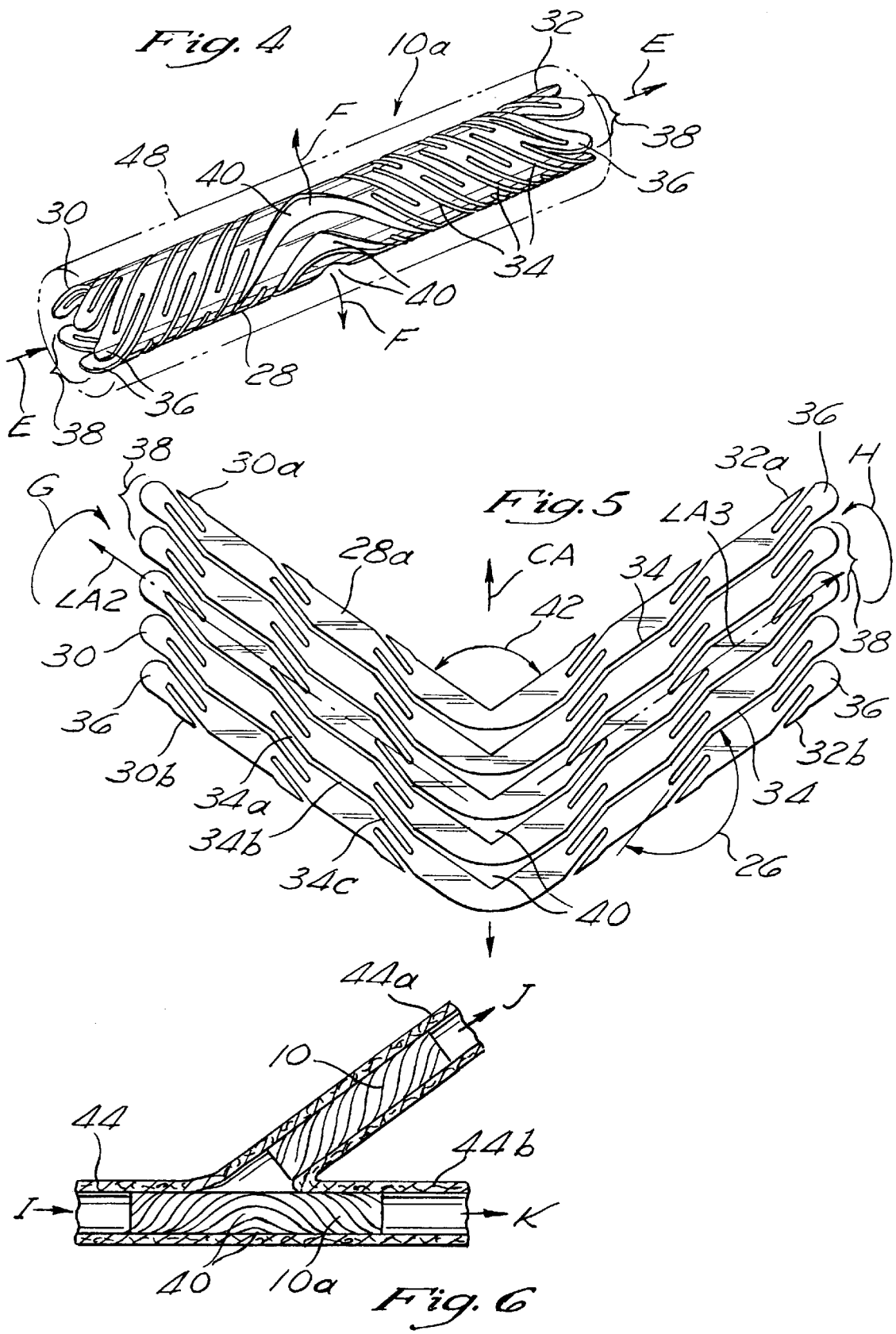

CORONARY STENT AND METHOD OF FABRICATING SAME

FIELD OF THE INVENTION

The present invention relates generally to medical devices, and more particularly, to expandable intraluminal stents for treating narrowing of coronary or peripheral vessels.

BACKGROUND OF THE INVENTION

Cardiovascular disease, including atherosclerosis, is a leading cause of death in the United States. In response thereto, the medical community has developed a number of methods for treating coronary heart disease, some of which are specifically designed to treat the complications resulting from atherosclerosis and other forms of coronary arterial narrowing.

The most significant and well-known development in treating atherosclerosis, as well as other forms of coronary narrowing, is percutaneous transluminal coronary angioplasty, more commonly known and hereinafter referred to simply as "angioplasty". The objective in angioplasty is to enlarge the lumen of the affected coronary artery by imparting a radially expansive force, typically accomplished by inflating a balloon, within the narrowed lumen of the coronary artery.

While the affected artery can be effectively enlarged via angioplasty, however, in some instances the vessel restenosis chronically, or closes down acutely, negating the positive effect of the angioplasty procedure. In such cases, such restenosis has frequently necessitated repeat angioplasty procedures or open heart surgery. While such restenosis does not occur in the majority of patients, it does occur with enough frequency that such complications comprise a significant percentage of the overall failures of the angioplasty procedure.

To lessen the risk of restenosis, various devices have been proposed for mechanically keeping the affected vessel open after completion of the angioplasty procedure. Such mechanical endoprosthetic devices, which are generally referred to as stents, are typically inserted into the vessel, positioned across the narrowed portion of the vessel, and then extended to keep the passageway clear. Effectively, the stent overcomes the natural tendency of the vessel walls of some patients to close back down, thereby maintaining a more normal flow of blood through that vessel than would otherwise be possible if the stent were not in place.

Various types of stents have been proposed and can typically be classed into one of two categories. In the first class, the stents comprise various tubular metallic cylinders expanded by balloon dilatation when positioned across the region or portion of vessel to be widened. In the second class, the stents are formed of a heat expandable material, such as nitinol or elgiloy, that are formed to assume a radially expanded state when deployed at the afflicted area within the lumen of the vessel. In this regard, such stents are typically delivered to the affected area on a catheter capable of receiving heated fluids, such as heated saline, such that once properly positioned, the heated fluid is passed through the catheter, thus causing the stent to expand.

Regardless of the class, significant difficulties have been encountered with all prior art stents. Each has had its percentage of thrombosis, restenosis and tissue in-growth, as well as varying degrees of difficulty in deployment. Another difficulty with at least some prior art stents is that they do not readily conform to the vessel shape and/or do not accommodate bifurcated blood flow caused by vessels having collateral vessels extending therefrom. Importantly, virtually all prior art stents suffer from the drawback of being structurally incompetent to withstand the stress and strain when the axially expansive, dilatory force is imparted thereto. This latter deficiency is especially problematic insofar as the incapability of such stents to withstand the stress of an axially expansive force may cause the stent to structurally deteriorate and axially constrict over time or, alternatively, migrate from the section of lumen where the stent was deployed.

As such, because of these and other complications, there has resulted a low level of acceptance of such stents within the medical community, and to date, such stents within the medical community have not been accepted as a practical method for treating chronic restenosis.

Thus, there has been a long felt need for a stent which is effective to maintain a vessel open, which may be easily delivered to the affected area, easily expanded to the desired size, easily conform to the afflicted vessel, capable of treating curved vessels with collateral vessels extending therefrom, as well as withstand the stress and strain when an axially expansive force is imparted thereto.

SUMMARY OF THE INVENTION

The present invention substantially reduces the complications and overcomes the limitations of the prior art devices. In this respect, the present invention provides for expandable intraluminal stents characterized by stronger construction than prior art stents. In a first embodiment, the stent comprises a tubular shaped member having first and second ends that define an axial passageway therethrough. The tubular shaped member has a multiplicity of selectively shaped slots helically formed thereabout that are preferably provided in rows wherein the slots of each row are arranged in an end to end fashion. In an alternative embodiment, the stent is further provided with a plurality of openings axially formed about a portion of the stent that cooperate to define a series of radial passageways. Such radial passageways provide for the flow of fluid through the stent in a bifurcated manner. In both embodiments, the tubular shaped member is initially disposable in a radially collapsed configuration such that the device may be passed into the lumen of a blood vessel, and subsequently expanded to an operative configuration where it will frictionally engage the surrounding vessel wall to hold the device in fixed position within the blood vessel lumen.

The present invention further comprises methods of forming the aforementioned stents. In a first preferred method, the stents are formed by laser cutting or etching, the latter preferably by electronic discharge etching, the multiplicity of slots and openings upon a tubular member. Alternatively, the stents are formed from a rolled sheet of flattened material having such slots and openings formed thereon. With respect to the latter method, the stent according to a first preferred embodiment is formed from a sheet of material configured as a parallelogram extending diagonally along a longitudinal axis. The stent according to the second preferred embodiment of the present invention, in contrast, is fabricated from a sheet having a generally chevron-like shape.

The stents in accordance with the present invention may be deployed through conventional methods including deployment via a balloon catheter whereby the stent is positioned upon an inflatable balloon while the stent is maintained in its radially collapsed configuration and there-after radially expanded, via inflation of the balloon, such that the stent radially engages in a wall of an anatomical passageway. Alternatively, the stents may be deployed by advancing the same through the lumen of a conventional catheter such that the stent, once axially advanced through the lumen of the catheter at the distal-most end thereof, assumes the expanded configuration and thus remains axially seated within a portion of an anatomical passageway.

BRIEF DESCRIPTION OF THE DRAWINGS

These, as well as other features of the present invention, will become more apparent upon reference to the drawings wherein:

FIG. 1 depicts a perspective view of an endovascular stent according to a first preferred embodiment of the present invention;

FIG. 2 is a perspective view of a tubular structure utilized to fabricate the stent depicted in FIG. 1;

FIG. 3 is a side view of the stent of FIG. 1 wherein said stent is in an unrolled, flattened configuration;

FIG. 4 is a perspective view of an endovascular stent constructed according to a second preferred embodiment;

FIG. 5 is a side view of the stent of FIG. 4 wherein said stent is in an unrolled, flattened configuration; and FIG. 6 is a cross-sectional view of a bifurcating vessel having the stent depicted in FIG. 1 and the stent depicted in FIG. 4 intraluminally disposed therewithin.

DETAILED DESCRIPTION OF THE PREFERRED EMBODIMENT

The detailed description set forth below in connection with the appended drawings is intended merely as a description of the presently preferred embodiments of the invention, and is not intended to represent the only form in which the present invention may be constructed or utilized. The description sets forth the functions and sequence of steps for construction and implementation of the invention in connection with the illustrated embodiments. It is to be understood, however, that the same or equivalent functions and sequences may be accomplished by different embodiments that are also intended to be encompassed within the spirit and scope of the invention.

Referring now to FIG. 1, there is perspectively illustrated a stent device 10 constructed in accordance with a first preferred embodiment of the present invention. As is well-known in the art, and as will be discussed in more detail below, the stent 10 may be utilized to reinforce or dilate numerous types of anatomical passageways, including blood vessels, urogenital passageways and bioducts. In relation to cardiovascular applications, the stent 10 is typically inserted into a blood vessel to dilate areas of the vessel which have become occluded by atherosclerotic plaque or constricted by an adjacent tumor.

As shown, the stent 10 comprises an elongate tubular shaped member 12 having a first end 14 and second end 16 that define an axial pathway therethrough, as indicated by the letter A therethrough. Helically formed about tubular shaped member 12 are a multiplicity of uniformly shaped slots 18. The slots 18 are preferably formed about tubular shaped member 12 in rows extending in parallel relation to one another, whereby the slots 18 in each such row are oriented in an end to end fashion.

In a preferred embodiment, each slot of said multiplicity of slots is generally formed to have first, second and third elongate segments, more clearly seen as 18a, 18b and 18c, respectively, of FIG. 3. As shown, second segment 18b is disposed intermediate first and third segments 18a, 18c with first and third segments 18a, 18c extending in opposed directions therefrom such that first and third segments 18a, 18c are maintained in generally parallel relation to one another. Preferably, segments 18a and 18c are formed to extend from second segment 18b at an angle 26, which preferably ranges from 160° to 165°. As will be appreciated by those skilled in the art, the lengths of segments 18a, 18b, 18c may be selectively varied to provide the stent 10 a wider range of expandability, as discussed below.

By virtue of the helical arrangement of rows of slots 18 having the aforementioned configuration, there is thus formed a plurality of bends 20 about the first and second ends 14, 16 of tubular shaped structure 12. Such plurality of bends 20 are disposed in generally parallel, convoluted relation to one another that there is thus defined a multiplicity of serpentine convolutions 22 at each respective end 14, 16 of the tubular shaped member 12.

As will be recognized by those skilled in the art, the tubular shaped structure 12 will be specifically designed and configured to assume a first radially collapsed configuration as shown, such that the device may be passed into and selectively positioned within the lumen of a vessel, and subsequently expanded to an operative configuration, shown in phantom as 46, wherein such structure 12 will frictionally engage the surrounding blood vessel wall to hold the device 10 in fixed position therewithin. In order for the device 10 to assume both a radially collapsed configuration and second expandable or operative configuration, such device may be fabricated from a shape memory material, such as nitinol, which thus enables the device to assume the collapsed configuration when at room temperature, but which transitions to the operative configuration when warmed to body temperature, as will occur when such device is deployed.

Alternatively, the stent of the present invention may be formed of resilient, self-expanding material which is biased to the operative configuration such that when unconstrained, the device will resiliently self-expand to the expanded, operative configuration. Still further, the device may be fabricated from a plastically deformable material which is initially formed to assume a radially compact configuration, but which can subsequently be deformed to assume the expanded, operative configuration by application of pressure, such as a balloon catheter discussed more fully below, against such stent. Among the biologically compatible materials that may be utilized to construct the stents disclosed herein include stainless steel, titanium, tantalum, nickel titanium, elgiloy, and high strength thermoplastic polymers.

Advantageously, by providing such convolutions 22 at the respective ends 14, 16 of the tubular shaped structure 12, the stent 10 is provided greater structural stability and capacity to withstand axially compressive stress within the lumen of a vessel when the tubular shaped structure 12 is expanded to its operative configuration than prior art stent devices. In this regard, such convolutions 22, by virtue of their angled, convoluted configuration, tend to cause ends 14, 16 to radially expand in a rotational manner whereby the stress of such radial expansion about ends 14, 16 is more strategically placed and evenly distributed about segments 20a, as shown in FIGS. 1 and 3. The helical arrangement of slots 18 further enables the tubular structure 12, by virtue of its radial expansion in a rotational manner, to assume a wider range of expandability when maintained in the operative configuration. As will be recognized and appreciated by those skilled in the art, by increasing the length of slot 18, the tubular structure 12 will thus be provided with a selectively wider range of expandability. Other prior art devices, in contrast, most notable of which being zig-zag type stents, tend to expand in a non-rotational manner and thus store stress in their respective joints or apices when radially expanded. As a result, such prior art stents are prone to structurally deteriorate over time.

Referring now to FIGS. 2 and 3, there is shown two preferred methods of fabricating the stent 10 of the present invention. Referring firstly to FIG. 2, there is perspectively shown tubular shaped member 12a in an unaltered state. As is well-known to those skilled in the art, the stent 10 depicted in FIG. 1 may be formed from tubular shaped member 12a by forming the helically disposed rows of slots by a laser, such as a YAG laser, or by electronic discharge etching, as formed by an electronic discharge machine.

FIG. 3 depicts an alternative method of fabricating the stent 10 of the present invention by forming the same from an elongate sheet of flattened, biologically compatible material 12b. In order for the sheet 12b to assume a tubular configuration, the sheet 12b must necessarily be configured as an elongate parallelogram having first and second ends 14, 16, and thereby defining four end portions or corners 14a, b, that extends diagonally along a longitudinal axis LA1. In the preferred embodiment, the sheet 12b will extend diagonally upward relative a vertical axis D at an angle 24 ranging from 50° to 55°, with an angle of 54°47' being most preferred. The multiplicity of slots 18 may then be formed upon sheet 12b in rows extending in parallel relation to one another along the longitudinal axis LA1. As discussed above, the slots 18 will preferably be arranged in an end to end fashion and further, will preferably be formed of angled segments 18a, 18b and 18c, as discussed above.

To cause sheet 12b to assume a tubular configuration, the opposed ends 14, 16 of the sheet 12b are rotated in the direction shown by the letters B and C. More specifically, bottom end portion or corner 14a of end 14 will be rotate in the direction indicated by the letter B such that end portion 14a mates with and is fused, preferably by laser welding, resistance welding, soldering, brazing or other joining methods known in the art, to complementary end portion 14b. Concurrently with the rotation and fusion of end portions 14a and 14b, end portion 16a of end 16 will be rotated in the direction indicated by the letter C such that such portion mates with and is fused to complementary portion 16b. The stent 10 of FIG. 1 will thus be formed and the same can be deployed in the manner discussed below.

Referring now to FIG. 4, there is perspectively illustrated an alternative embodiment 10a of the stent of the present invention. Embodiment 10a is specifically designed and adapted for insertion into a bifurcating vessel to thus accommodate and facilitate the flow of blood into off-shoot directions. Similar to the first embodiment, the second embodiment 10a comprises a corresponding tubular shaped member 28 having first and second ends 30, 32 defining an axial passageway, depicted by the letter E, therethrough that likewise is designed to assume a first radially collapsed configuration as shown, and a second expanded or operative configuration shown in phantom 48. The stent 10a according to the second embodiment further includes a multiplicity of helically arranged rows of uniformly shaped slots 34. However, the multiplicity of slots 34, according to the second embodiment, are helically arranged in different rotational directions such that the slots emanating from first end 30 have an opposite rotational orientation than slots emanating from second end 32. Notwithstanding, the ends 30, 32 of the second embodiment 10a of the stent of the present invention, as with the first embodiment, are characterized by a plurality of bends 36 disposed in generally parallel, convoluted relation to one another such that a multiplicity of serpentine convolutions 38 are formed.

To provide for the flow of blood in an offshoot direction, stent 10a further includes a plurality of generally chevron-shaped openings 40 axially disposed about a portion of a tubular-shaped structure 28 and between the helically arranged slots emanating from end 30 and 3nd 32. As will be recognized, such plurality of openings 40 thus creates a series of radial passageways F that, as will be discussed below, enable blood to flow to an off-shoot vessel, in addition to allowing a portion of the blood to flow axially through the tubular structure 28 as indicated by the letter E.

The stent 10a according to the second embodiment may be formed by etching, via electronic discharge etching, the multiplicity of slots 34 and openings 40 about a tube of biologically compatible material, such as 12a depicted in FIG. 2.

The stent 10a according to the second embodiment may further be fabricated from a sheet of flattened, biologically compatible material 28a as depicted in FIG. 5. As will be recognized, in order for such sheet 28a to assume a tubular structure and likewise provide for the series of radial passageways F, such sheet 28a must be provided to have a generally chevron-like configuration that defines a first end 30, having end portions or corners 30a, 30b, and a second end 32, having end portions or corners 32a, 32b.

As with the first embodiment, the multiplicity of slots 34 may be formed upon the sheet 28a in a similar manner and according to the same structure as slots 18 formed upon first embodiment 10. However, by virtue of the generally chevron-like shape of the sheet 28a, it will be necessary to form the multiplicity of slots such that a first multiplicity of slots are formed upon sheet 28a in rows extending in parallel relation to one another along longitudinal axis LA2, and a second multiplicity of slots formed upon sheet 28a that extend in parallel relation to one another along longitudinal axis LA3. In a preferred embodiment, longitudinal axis LA2 will extend in a radially opposed direction than longitudinal axis LA3 at an angle 42 of approximately 109°35'. Intermediate the rows of slots extending along longitudinal axes LA2 and LA3 and along the central axis CA of sheet 28a will be formed openings 40. As will be recognized, such openings 40 shall be arranged in a generally linear manner.

In order for the stent 10a according to the second embodiment to achieve a generally tubular configuration, it will be necessary that the respective ends thereof 30, 32 be rotated in the directions indicated by the letters G and H such that the configuration as shown in FIG. 4 is achieved. Specifically, end portion 30a of end 30 is rotated in the direction indicated by the letter G such that end 30a mates with and is fused to the end portion 30b of end 30. Similarly, in the portion 32a of end 32 is rotated in the direction indicated by the letter H such that the same mates with and is fused to end portion 32b the resultant structure assumes a generally cylindrical structure as depicted in FIG. 4.

The stents according to either preferred embodiment 10, 10a may be deployed by any of several well-known techniques. In this regard, stents 10, 10a disclosed herein may be deployed via a balloon catheter whereby the stent is positioned upon an inflatable balloon while the stent is maintained in its radially collapsed configuration such that the balloon may be transluminally advanced through an anatomical passageway to a desired treatment site, such as one including an atherosclerotic plaque occlusion. After the positioning of such balloon at the desired treatment site, thus causing the stent to radially expand from its radially compressed configuration to is operative configuration, which in turn causes the stent 10, 10a to radially engage the inner wall of an anatomical passageway, such as 44, 44a and 44b depicted in FIG. 6. The balloon will then be deflated, with the balloon catheter being removed within the anatomical passageway such that the stents 10, 10a remain operatively positioned at selected sites therewithin.

Alternatively, should the stents 10, 10a of the present invention be fabricated from a sheet memory or self-expanding material, such stents may be deployed using a conventional catheter. As is known in the art, such catheters typically have a lumen formed therein through which stents, such as those of the present invention, may be deployed at a desired site. In this regard, such stents may be loaded within the lumen of the catheter and advanced therethrough via a pusher. Once the desired site to be transluminally reinforced is accessed by the distal end of the catheter, the stent is then advanced through the lumen of the distal end of the catheter where the same remains resident.

As depicted in FIG. 6, once maintained in position, stents 10 and 10a will enable blood to flow freely therethrough. In particular, stent 10a according to the second preferred embodiment will enable blood to flow initially from the direction indicated by the letter I in a bifurcated manner represented by the letters K and J. Stent 10, as axially nested within a portion of anatomical passageway 44a will thus allow blood to flow in a unidirectional manner as indicated by the letter J.

Although the invention has been described herein with specific reference to presently preferred embodiments thereof, it will be appreciated by those skilled in the art that various additions, modifications, deletions and alterations may be made to such preferred embodiments without departing from the spirit and scope of the invention. Accordingly, it is intended that all reasonably foreseeable additions, modifications, deletions and alterations be included within the scope of the invention as defined in the following claims.

What is claimed is:

1. An expandable intraluminal stent comprising:
   a) a tubular shaped member having first and second ends defining an axial passageway therethrough, said tubular shaped member having a multiplicity of slots helically formed thereabout wherein each slot of said multiplicity of slots is formed to have a first elongate segment, a second intermediate elongate segment, and a third elongate segment, said second elongate segment being disposed said intermediate said first and third segments, said slots being provided in rows wherein the slots of each respective row are arranged in an end to end fashion; and
   b) wherein said tubular shaped member is initially disposed in a first radially collapsed configuration such that said tubular member may be passed into the lumen of a blood vessel, and subsequently expanded to a second operative configuration wherein said tubular member will frictionally engage the surrounding blood vessel wall to hold said tubular member in fixed position within said blood vessel lumen.

2. The expandable intraluminal stent of claim 1 wherein said multiplicity of slots are so helically disposed about said tubular structure that the first and second ends of said structure assume a serpentine configuration.

3. The expandable intraluminal stent of claim 2 wherein said stent further includes a multiplicity of openings radially formed about a segment of said tubular shaped member, said openings being so radially positioned about said tubular shaped member such that a series of radial passageways are formed thereabout.

4. The expandable intraluminal stent of claim 1 wherein said stent is formed of a shaped memory material which assumes said collapsed configuration when at room temperature and which transitions to said operative configuration when warmed to body temperature.

5. The expandable intraluminal stent of claim 1 wherein said stent is formed of resilient, self-expanding material which is biased to said operative configuration such that, when unconstrained, said stent will resiliently self-expand to said operative configuration.

6. The expandable intraluminal stent of claim 1 wherein said stent is formed of a plastically deformable material which is initially of said radially compact configuration, but which is subsequently deformable to said operative configuration by the application of pressure against said stent.

7. The expandable interluminal stent of claim 1 wherein said stent is constructed from a unitary piece of non-welded material.

8. The expandable interluminal stent of claim 1 wherein said stent is positionable upon a balloon catheter assembly such that said stent may be positioned at a desired site in the lumen of said blood vessel, said stent being designed to transition from said first collapsed configuration to said second operative configuration upon expansion of said balloon.

9. An expandable interluminal stent comprising:
   a) a tubular shape member having first and second ends defining an axially passageway therethrough, said tubular shape member having a multiplicity of slots helically formed thereabout wherein each slot of multiplicity of slots is formed to have a first elongate segment, second elongate segment, and third elongate segment, said second elongate segment being disposed intermediate said first and third segments, said first and third segments extending outwardly from said second segment at an angle between 160 degrees and 165 degrees, said first and third segments so extending from said second segment that said first and third segments extend in generally parallel relation to one another, said slots being provided in rows wherein the slots of each respective row are arranged in an end to end fashion; and
   b) wherein said tubular shape member is initially disposed in a first radially collapsed configuration such that said tubular member may be passed into the lumen of a blood vessel, and subsequently expanded to a second operative configuration wherein said tubular member will frictionally engage the surrounding blood vessel wall to hold the device in a fixed position within said blood vessel lumen.

* * * * *